(12) United States Patent
Reuter

(10) Patent No.: US 6,436,094 B1
(45) Date of Patent: Aug. 20, 2002

(54) ELECTROMAGNETIC AND LASER TREATMENT AND COOLING DEVICE

(75) Inventor: Eric M. Reuter, Los Gatos, CA (US)

(73) Assignee: Laserscope, Inc., San Jose, CA (US)

( * ) Notice: Subject to any disclaimer, the term of this patent is extended or adjusted under 35 U.S.C. 154(b) by 0 days.

(21) Appl. No.: 09/527,052

(22) Filed: Mar. 16, 2000

(51) Int. Cl.[7] .............................................. A61B 18/20
(52) U.S. Cl. .............................. 606/9; 606/20; 606/25
(58) Field of Search ................................ 606/9–26, 33; 607/89, 101, 102

(56) References Cited

U.S. PATENT DOCUMENTS

| 3,821,510 A | 6/1974 | Muncheryan | 219/121 |
| 3,967,627 A | 7/1976 | Brown | 128/400 |
| 4,140,130 A | 2/1979 | Storm, III | 128/404 |
| 4,316,467 A | 2/1982 | Muckerheide | 128/303.1 |
| 4,388,924 A | 6/1983 | Weissman et al. | 128/303.1 |
| 4,733,660 A | 3/1988 | Itzkan | 128/303.1 |
| 4,832,024 A | 5/1989 | Boussignac et al. | 128/303.1 |
| 5,057,104 A | 10/1991 | Chess | 606/9 |
| 5,059,192 A | 10/1991 | Zaias | 606/9 |
| 5,066,293 A | 11/1991 | Furumoto | 606/9 |
| 5,226,907 A | 7/1993 | Tankovich | 606/133 |
| 5,249,192 A | 9/1993 | Kuizenga et al. | 372/23 |
| 5,272,716 A | 12/1993 | Soltz et al. | 372/109 |
| 5,282,797 A * | 2/1994 | Chess | 606/9 |
| 5,287,380 A | 2/1994 | Hsia | 372/69 |
| 5,330,519 A | 7/1994 | Mason et al. | 607/104 |
| 5,344,418 A | 9/1994 | Ghaffari | 606/9 |
| 5,405,368 A | 4/1995 | Eckhouse | 607/88 |
| 5,423,803 A | 6/1995 | Tankovich | 606/9 |
| 5,425,728 A | 6/1995 | Tankovich | 606/9 |
| 5,482,172 A | 1/1996 | Braddock | 215/235 |
| 5,486,172 A * | 1/1996 | Chess | 606/20 |
| 5,522,813 A | 6/1996 | Trelles | 606/2 |
| 5,531,740 A | 7/1996 | Black | 606/9 |

(List continued on next page.)

FOREIGN PATENT DOCUMENTS

| DE | 4434617 A1 | 4/1996 | A46B/7/04 |
| EP | 029051 A2 | 12/1988 | A46B/9/04 |
| EP | 0724866 A1 | 8/1996 | A61B/17/36 |
| WO | WO96/18433 | 6/1996 | A61N/5/06 |
| WO | WO96/22813 | 8/1996 | A61N/5/06 |
| WO | WO96/24182 | 8/1996 | H01S/3/213 |
| WO | WO96/33538 | 10/1996 | H01S/3/16 |
| WO | WO 97/37723 | 10/1997 | A61N/5/06 |

Primary Examiner—Lee Cohen
Assistant Examiner—H M Johnson
(74) Attorney, Agent, or Firm—Dorsey & Whitney LLP

(57) ABSTRACT

An apparatus for lowering the temperature of skin on a patient during treatment applying electromagnetic energy to the skin comprising a window of a first thermally conductive material through which electromagnetic energy can pass for placement against the epidermis of the skin. A reservoir of coolant is spaced from an edge of the window. A non-flowing second thermally conductive material connects the window and the reservoir to transfer heat from the window to the coolant in the reservoir.

38 Claims, 2 Drawing Sheets

U.S. PATENT DOCUMENTS

| | | | |
|---|---|---|---|
| 5,558,666 A | 9/1996 | Dewey et al. | 606/9 |
| 5,558,667 A | 9/1996 | Yarborough et al. | 606/9 |
| 5,578,029 A | 11/1996 | Trelles et al. | 606/25 |
| 5,595,568 A | 1/1997 | Anderson et al. | 606/9 |
| 5,599,342 A | 2/1997 | Hsia et al. | 606/9 |
| 5,611,357 A | 3/1997 | Suval | 128/898 |
| 5,624,435 A | 4/1997 | Furumoto et al. | 606/10 |
| 5,628,744 A | 5/1997 | Coleman et al. | 616/12 |
| 5,630,811 A | 5/1997 | Miller | 606/9 |
| 5,632,741 A | 5/1997 | Zavislan et al. | 606/9 |
| 5,647,866 A | 7/1997 | Zaias et al. | 606/9 |
| 5,653,706 A | 8/1997 | Zavislan et al. | 606/9 |
| 5,669,916 A | 9/1997 | Anderson | 606/133 |
| 5,695,495 A | 12/1997 | Ellman et al. | 606/41 |
| 5,735,844 A | 4/1998 | Anderson et al. | 606/9 |
| 5,743,901 A | 4/1998 | Grove et al. | 606/9 |
| 5,752,948 A | 5/1998 | Tankovich et al. | 606/9 |
| 5,754,573 A | 5/1998 | Yarborough et al. | 372/22 |
| 5,758,665 A | 6/1998 | Suval | 128/898 |
| 5,769,844 A | 6/1998 | Ghaffari | 606/16 |
| 5,792,168 A | 8/1998 | Suval | 606/185 |
| 5,810,801 A | 9/1998 | Anderson et al. | 606/9 |
| 5,814,040 A | 9/1998 | Nelson et al. | 606/9 |
| 5,820,626 A * | 10/1998 | Baumgardner | 606/13 |
| 5,830,208 A * | 11/1998 | Muller | 606/9 |
| 5,849,029 A * | 12/1998 | Eckhouse et al. | 607/104 |
| 5,853,407 A | 12/1998 | Miller | 606/9 |
| 5,868,732 A * | 2/1999 | Waldman et al. | 606/9 |
| 5,871,480 A | 2/1999 | Tankovich | 606/9 |
| 5,879,326 A | 3/1999 | Godshall et al. | 604/51 |
| 5,879,346 A | 3/1999 | Waldman et al. | 606/9 |
| 5,911,718 A | 6/1999 | Yarborough et al. | 606/9 |
| RE36,634 E * | 3/2000 | Ghaffari | 606/9 |
| 6,059,820 A * | 5/2000 | Baronov | 607/89 |
| 6,104,959 A * | 8/2000 | Spertell | 607/101 |
| 6,264,649 B1 * | 7/2001 | Whitcroft et al. | 606/22 |

* cited by examiner

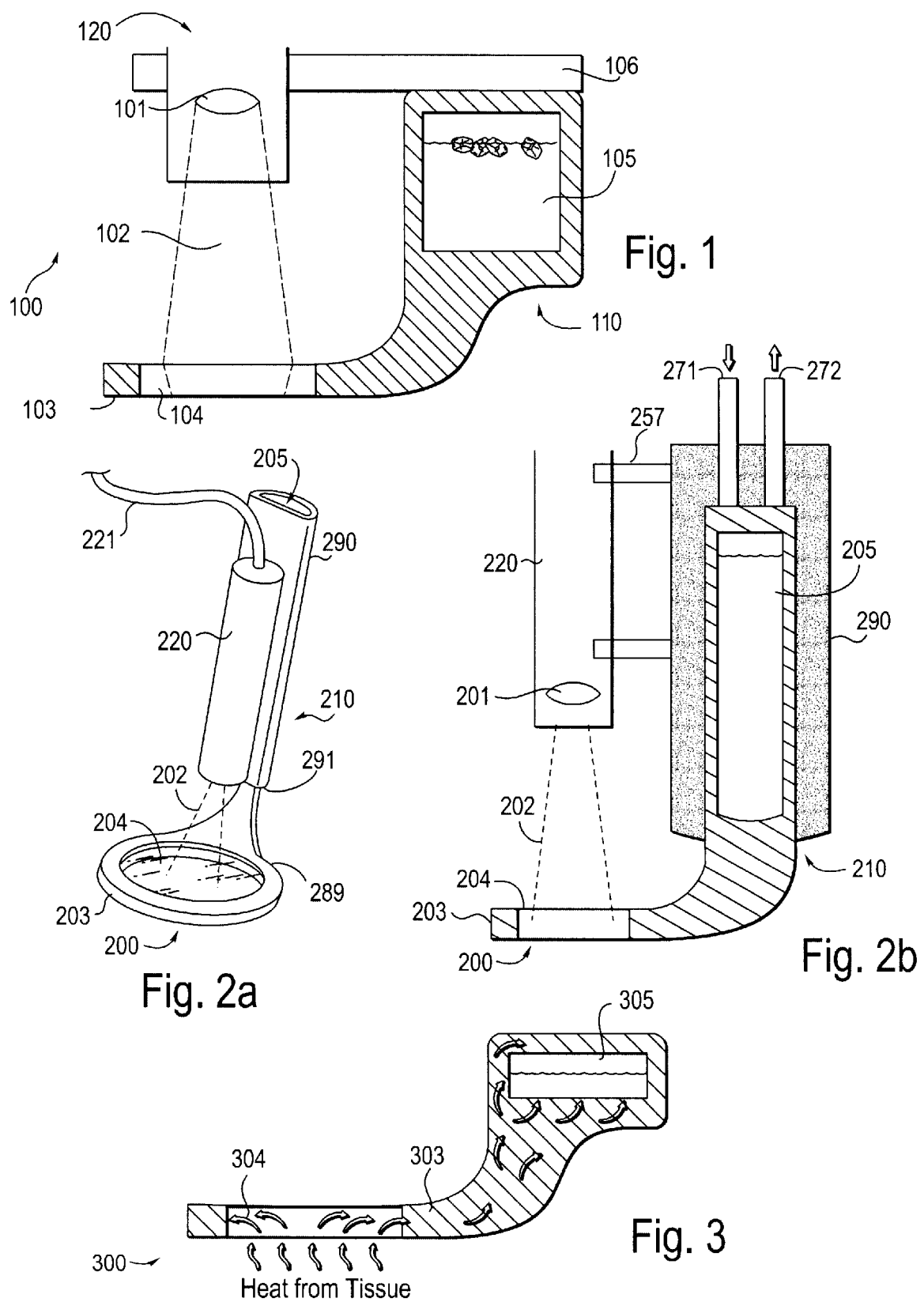

ELECTROMAGNETIC AND LASER TREATMENT AND COOLING DEVICE

TECHNICAL FIELD

This invention relates to electromagnetic and laser treatment devices and more particularly to a cooling apparatus for use with electromagnetic and laser devices to cool the human skin during the treatment of patients.

BACKGROUND

The method of treating cutaneous lesions with light sources such as lasers is primarily based on the principal of Selective Photothermolysis proposed by Anderson ("Selective Photothermolysis: Precise Microsurgery by Selective Absorption of Pulsed Radiation", Science, Volume 220, April 1983). This mechanism involves the selective absorption of light by various chromophores in the body. As these chromophores absorb the light energy, they heat up and destroy the surrounding tissue. This tissue destruction can be used as an alternative therapy to sclerotherapy in a beneficial way to remove unsightly veins and other vascular lesions since these lesions typically contain one or more highly absorbent chromophores.

The degree of selectivity and therefore tissue damage is dependent upon the type and amount of chromophore present in the tissue, the depth of the target in the tissue, and highly dependent upon the wavelength of the light being used. Since lasers are able to provide light in very precise wavelength regimes, lasers are ideal instruments for capitalizing on this principal for treatment of various lesions. This selectivity can be very beneficial in that specific lesions containing or surrounded by a particular chromophore(s) can be targeted with specific wavelengths to provide localized heating and damage while sparing surrounding tissue lacking the chromophore(s).

In practice however, the light absorption of different chromophores may be similar. For example, melanin, a chromophore which is found in the epidermis of the skin, may absorb a very similar amount of light energy at some wavelengths as the target tissue (such as the hemoglobin in a vein). Therefore, when attempting to deliver sufficiently large amounts of light energy to a target area such as a vein, the melanin in the skin above the target area may absorb enough light energy to cause epidermal damage to the skin before the target area has received sufficient energy to cause sufficient damage.

If this epidermal layer, however, is superficially cooled just prior to and/or during the application of the laser energy, the net change in temperature of the chromophores and tissue on the surface will be less and therefore the collateral damage will be less as well.

It has been known for quite some time that simple cooling techniques can be used to certain advantage in conjunction with certain therapies, including RF and laser therapies. Such simplistic cooling mechanisms include, for example, applying an ice bag to the target area for a predetermined time period prior to the application of therapeutic energy to the target area. It has also been prior described to precool the target area, as described above, and alternately provide therapeutic energy to the target area and a recooling of the target area.

It has been known for quite sometime that various cooling techniques can be used to protect the device used to provide treatment to a patient. U.S. Pat. No. 4,832,024, issued to Boussignak et al. is one such device in which a cooling fluid is flowed in a chamber between an optical fiber and the distal emitting end of a cardiovascular catheter. Various other prior art devices provide a similar cooling of the device, sometimes together with some resultant cooling of the patient target area. U.S. Pat. No. 4,733,660 issued to Itzkan is such a device in which a coolant is flowed at the distal end of a laser system, such that the laser light is passed through the liquid coolant, which is passed across the irradiated areas of the patient under treatment. U.S. Pat. No. 3,821,510 issued to Muncheryan provides a hand held laser instrumentation device in which cooling is achieved by evaporation when a coolant is sprayed from the laser device to the superficial tissue of the patient undergoing treatment. International Patent Publication WO 97-37723 similarly provides a cooling spray directly onto the tissue of the patient. U.S. Pat. Nos. 5,814,040 and 5,820,628 also spray gas and/or liquid directly onto the skin to provide cooling.

U.S. Pat. Nos. 5,057,104; 5,282,797; and 5,486,172 to Chess provide methods and apparatus for cooling the skin simultaneously with the delivery of laser light energy. Although lasers and cooling of the skin are involved and discussed, the devices described require a cooling fluid to reside over or be passed over the treatment site during laser treatment. This requires that the cooling medium be captured between two separate transparent windows which can impair visibility of the treatment area. Proper visualization of the treatment site is very important since many veins are smaller than 100 microns and difficult to target without excellent visibility of target site. A multi-layer fluid container assembly such as described is expensive, and can impair the ability of the practitioner to deliver the light to the appropriate target area.

Additionally, if not used correctly, these devices can cause relatively large refractive changes in both the incoming laser light (changing the delivered treatment spot size and therefore the treatment fluences) and in the visible light leaving the target area (making it difficult to aim the treatment beam correctly).

U.S. Pat. No. 5,344,418 to Ghaffari provides a system with a thermally conductive optical window which is cooled on one side by a cooled gas (carbon dioxide and Freon™ are mentioned) and in contact with the skin on the other. This system is described to be used in combination with a feedback mechanism to control laser light delivery to the treatment site. The cooling mechanism described requires the use of complex delivery equipment and expensive (and possibly) environmentally hazardous) materials.

U.S. Pat. No. 4,140,130 to Storm provides a RF system with a cooling electrode used to direct RF energy to the target and to keep the skin cool. However, this system also calls for the cooling fluid to flow over the target area where the energy is being delivered and relates to RF devices, not to lasers.

U.S. Pat. No. 3,967,627 to Brown provides a heating and cooling applicator and control and monitoring circuitry for cooling and heating areas of the body. This device is not used for laser therapy and also has the cooling fluid passing over the entire contact area to be cooled.

SUMMARY

It is an object of this invention to provide a simple device to cool the skin during treatment with electromagnetic energy, including treatment of vascular and cutaneous lesions, skin disorders, and the removal of hair.

It is another object of this invention to decrease the complexity of the existing art and to provide a more economical, cost-effective, and easy to use device. This is accomplished in one embodiment by using a thermodynamic property of water or other material called the "latent heat of fusion" to provide a temporary but relatively constant temperature at the treatment window.

It is still further an object of the present invention to provide a simpler, easier means of visualizing and cooling the target treatment zone while simultaneously delivering the electromagnetic energy.

It is yet another object of the invention to provide an apparatus which can be used for cooling the skin during treatment with electromagnetic energy in areas which are difficult to access with existing art such as the areas around the nose and ankles.

BRIEF DESCRIPTION OF THE DRAWINGS

FIG. 1 is a cross sectional view of one embodiment of the invention;

FIG. 2a is a perspective view of another embodiment of the invention;

FIG. 2b is a cross sectional view of the embodiment of FIG. 2a;

FIG. 3 is a schematic view of the heat transfer mechanism of various embodiments.

DETAILED DESCRIPTION

Figure 4:
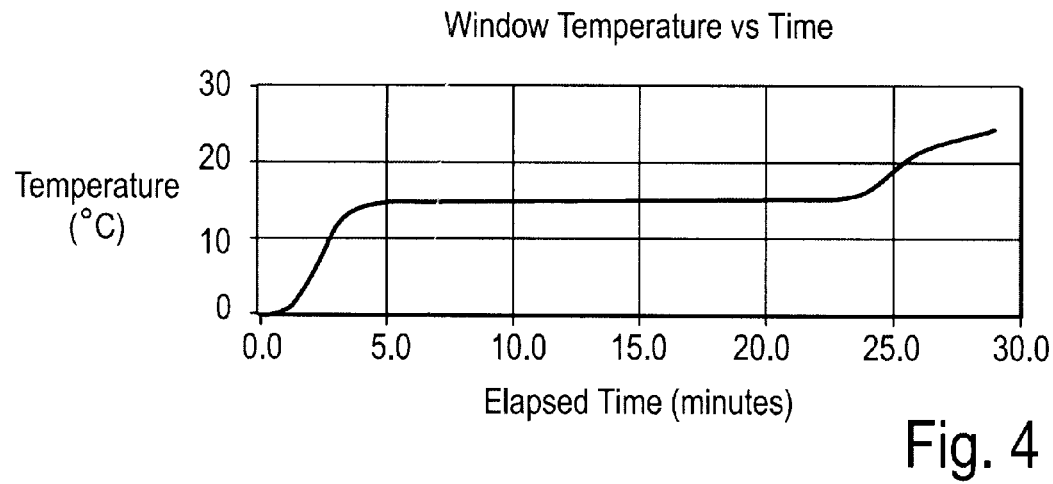
FIG. 4 is a graph depicting temperature verses time for an embodiment of this invention.

The mechanisms for heating the desired tissues during treatment with electromagnetic energy have been described and it is now established in the practice that cooling the skin during such treatment reduces patient discomfort, allows for higher treatment fluences, and increases the efficacy of the treatment. Such treatments include a treatment of an epidermal layers of the skin, to treat skin disorders, hair removal, and the treatment of vascular and pigmented lesions.

FIG. 1 is a cross-sectional view depicting one embodiment of this invention. FIG. 1 depicts system 100 which includes an energy exit port 101, such as a lens or the end of an optical fiber, at the distal end of a delivery device 120, and a cooling device 110. Cooling device 110 allows cooling of the skin in conjunction with exposure to electromagnetic energy, including laser energy. Such cooling may take place before, during, and/or after such exposure to electromagnetic energy.

Port 101 emits electromagnetic energy, such as laser energy, 102, which is generated in any convenient manner well known to those of ordinary skill in the art. Energy 102 is directed to a patient target area through cooling window 104 of cooling device 110, which in operation is placed against the area of the patient to be treated. Cooling window 104 is in direct contact with the patient's skin, or in contact with the skin via a liquid, gel, or membrane. Cooling window 104 is constructed of a material which is tough yet inexpensive, and provides good thermal conductivity and low absorption of energy 102. Preferably, the material used to construct window 104 is not hydroscopic. Suitable materials for window 104 include many glasses known to those in the laser industry including quartz, including polymorphic glass, undoped YAG, diamond, and sapphire, for example being largely transparent to a variety of electromagnetic energy 102, for example laser energy in the wavelength range between about 0.2 to 3.5 microns. In certain embodiments, a range of 400 to 1100 nanometers is used. If desired, window 104 is coated on one or both sides with an anti-reflective coating. Preferably, window 104 allows excellent visualization during the procedure, is scratch resistant and is small enough to treat highly contoured areas, such as those on the face and nose.

Surrounding window 104 is a thermally conductive material 103 which, in the embodiment of FIG. 1, is thermally coupled to a thermal reservoir 105. Thermal reservoir 105 acts as a heat sink and comprises, for example, a mass of thermally conductive material, if desired the same material used to form thermally conductive material 103. In another embodiment, thermal reservoir 105 is a cavity containing coolant medium which is chilled prior to the use of cooling device 110. In one embodiment, thermal reservoir 105 contains a fluid such as water and/or ice; carbon dioxide, hydrocarbons, fluorocarbon, chlorofluorocarbons, air, nitrogen, Freon™, gels, or other cooling solids and/or liquids and/or gasses, which is cooled to a desired temperature or, if desired, frozen prior to use of cooling device 110. In operation, window 104 absorbs very little energy 102 passing through it to the patient's skin. By way of example, if sapphire is used as the material for window 104, and window 104 is formed to a thickness of approximately 1 to 20 mm, only about less then one percent of laser energy is absorbed by window 104. This small amount of heat absorbed by window 104 is readily absorbed by thermally conductive material 103 surrounding window 104 so that the temperature of window 104 is not increased. More importantly, since window 104 absorbs very little energy from energy beam 102 such that its temperature does not rise to any significant degree during treatment of the patient, window 104 serves to conduct heat away from the patient's skin in the treatment area, thereby preventing discomfort to the patient and enhancing treatment efficacy by allowing a longer treatment period.

The size of thermal reservoir 105 is made to any convenient size consistent with convenient operator utilization and a desired amount of thermal cooling effect based upon the type of material forming thermal reservoir 105. For greater cooling ability, thermal reservoir 105 contains a material capable of changing state, such as, for example, water, which may be frozen prior to the treatment of the patient. During treatment of the patient, this frozen coolant contained within thermal reservoir 105 acts as an excellent coolant device and absorbs significant amounts of heat as the state changes from solid to liquid and the latent heat of fusion is absorbed by the coolant material during this change of state. Alternatively, gas such as air, nitrogen, $CO_2$, or a cryogenic gas is used as the coolant material. In other embodiments, a gas is used which is cooled to a liquid or solid state, allowing the latent heat of vaporization and/or the latent heat of fusion to be used in achieving the desired cooling effect.

The present invention has been designed specifically to cool the surface of the skin before, during and after laser exposures. Like other active cooling devices used in dermatology, the present invention significantly lowers the temperature of the epidermis and the dermal-epidermal junction. The lower temperature facilitates higher treatment fluences and reduces the thermal damage to non-target tissue, which significantly reduces side effects such as transitory hyper- or hypo-pigmentation. The present invention significantly reduces the pain experienced by patients. Unlike other cooling technologies, this embodiment of the present invention does not require the use of expensive cryogenic canisters or chillers and does not use cumbersome hoses to provide cooling. FIG. 3 shows a magnified cross sectional view of a cooling tip in contact with skin with arrows indicating the flow of heat from the epidermis, to the sapphire window and the cooling reservoir.

To fully appreciate the advantages of the present invention compared to other active cooling devices, it is important to understand how it works. One embodiment of the present invention utilizes the large latent heat of fusion of water (79.71 calories/gram) to maintain the skin at a constant low temperature for long periods of time. Because it requires so much energy to melt ice, the 13.1 grams of ice in the reusable tips have more heat capacity than 1.0 liters of liquid water at 0 degrees Celsius. As the ice melts, the temperature of the reservoir in the present invention is maintained at 0 degrees Celsius. for an average of 20 minutes under normal operating conditions. This allows the window of the present invention to maintain a constant temperature of 15° C. or lower, for 20 minutes, while being traced over the skin at a rate of 1 cm/second, in a 25° C. room, with 100 watts of laser light directed through the sapphire window. When used in this manner, most of the heat removed by the present invention is not from the laser light absorbed at tissue, but rather from ordinary body heat (approximately 0.2 to 1 calorie/second are transferred from the epidermis to the sapphire window). After 20 minutes have elapsed, the cooling tip can be easily replaced with another frozen cooling tip. Thus, the four cooling tips supplied with the present invention provide 1 hour and 20 minutes of cooling that can be "recharged" by placing them in a freezer for 30 minutes and thus, allowing continuous laser treatment. FIG. 4 shows the temperature of the window in one embodiment of the present invention which does not utilize any pipping or flowing of the coolant, over a 30 minute time interval. The constant temperature during the 4–24 minute time period is due to the presence of ice in the reservoir of this embodiment. Only after all the ice in the reservoir has melted does the temperature begin rising to room temperature.

In one embodiment, one or more temperature sensors are placed in thermal contact with one or more of window 104, thermally conductive material 103, and thermal reservoir 105. In one such embodiment, the temperature sensor is made of color changing liquid crystals or the like.

In one embodiment, system 100 includes, if desired, a bracket 106 such that the cooling device including cooling window 104 is attached to the distal end 101 of the delivery system, thereby allowing easy operator manipulation. In one embodiment bracket 106 is detachable from one or both of delivery system 120 and cooling device 110, to permit cooling device 110 to be easily removed for precooling, or use on other delivery systems.

In certain embodiments, a good thermal bond is made between cooling window 104 and surrounding thermally conductive material 103. Smooth surfaces to provide for a press or snap fit of window 104 into surrounding thermally conductive material 103 enhance thermal conductivity therebetween. In alternative embodiments, thermal epoxy, brazing, or soldering is used to secure cooling window 104 to thermally conductive material 103 and provide good heat transfer therebetween. In alternative embodiments, thermally conductive material 103 is plated with a low allergic reaction material, such as gold plated copper.

FIG. 2a is a perspective view of an alternative embodiment of the present invention. Electromagnetic energy system 200 of FIG. 2a includes electromagnetic energy delivery device 220 which receives energy, for example, laser energy, via optical fiber 221 and emits energy 202 from its distal end. Energy 202 is directed to a patient target area through cooling window 204 of cooling device 210. At least surrounding cooling window 204 is thermally conductive material 203 which conducts thermal energy from the patient's treatment area as such heat is absorbed by cooling window 204. The heat thus absorbed by cooling window 204 and by thermally conductive material 203 is conducted to thermal reservoir 205 contained within handpiece 290. Handpiece 290 of cooling device 210 is, if desired, attached to electromagnetic energy delivery device 220 such that system 200 is conveniently manipulated as a single unit. In one embodiment, this attachment is provided as a detachable engagement such that cooling unit 210 and electromagnetic energy deliverable device 220 can be separating for cleaning, maintenance, or the precooling of cooling device of 210 prior to use in a medical procedure. In one embodiment of this invention, cooling device 210 includes hand piece 290 which is detachably connected to cooling tip 289 via a detachable connection 291.

FIG. 2b depicts a cross sectional view of one embodiment of this invention similar to that shown in perspective view of FIG. 2a, with common reference numerals. As shown in FIG. 2b, electromagnetic energy delivery device 220 includes electromagnetic energy exit port 201, such as a lens or an optical fiber. The connection between the electromagnetic energy delivery device 220 and hand piece 290 is shown by reference numeral 250. As shown in FIG. 2b, hand piece 290 in this embodiment includes a thermal reservoir 205 which contains a cooling medium. In one embodiment, this cooling medium is self contained, and is cooled prior to use of cooling device 290. In this embodiment, the material contained within thermal reservoir 205 is formed of any convenient material capable of absorbing thermal energy, including various metals or the like. Alternatively, thermal reservoir 205 contains a liquid, such as water, or a gas such as air, nitrogen, $CO_2$, or cryogenic gas. As previously described, in certain embodiments material contained within thermal reservoir 205 is capable of changing state, thereby allow the latent heat fusion and/or the latent heat vaporization to be used to absorb thermal energy from the patient's skin via cooling window 204 and thermally conductive material 203.

In one embodiment, as depicted in FIG. 2b, an inlet port 271 and an outlet port 272 are used to circulate cooling material (i.e. liquid or gas) either directly into thermal reservoir 205, or to a chamber surrounding thermal reservoir 205, in order to allow cooling medium to be circulated to handpiece 290, in turn gathering thermal energy absorbed from a patient's skin. If desired, this cooling material is chilled and recirculated, for example by use of a chiller or thermoelectric cooler and pump system. Alternatively, cooling material is simply obtained from a cool source and disposed of after absorbing heat from cooling device 290.

FIG. 3 is a schematic representation of heat from a patent's tissue being absorbed by thermal window 304 and transmitted to thermally conductive material 303 for absorption by thermal reservoir 305.

As shown in FIG. 3, heat is absorbed from the patient's tissue by window 304 and conducted by thermal conductive material 303 to reservoir 305 containing coolant. As depicted in FIG. 3, in accordance with the teachings of the present invention, a simple and cost effective mechanism is provided for cooling patient's skin before, during, and/or after electromagnetic energy treatment, without the need for expensive and complex equipment, such as described in the prior art. Thus, no small and expensive tubes are required to pump coolant to regions directly surrounding the window. In contrast, in accordance with the teachings of this invention, a simple and cost effective structure is provided which adequately removes heat absorbed from the patient's tissue by the window, by simple thermal conductivity through non-flowing thermally conductive material to a coolant reservoir. The coolant reservoir contains adequate cooling capability to allow effective use in medical procedures without the need for expensive cooling arrangements.

Figure 5:
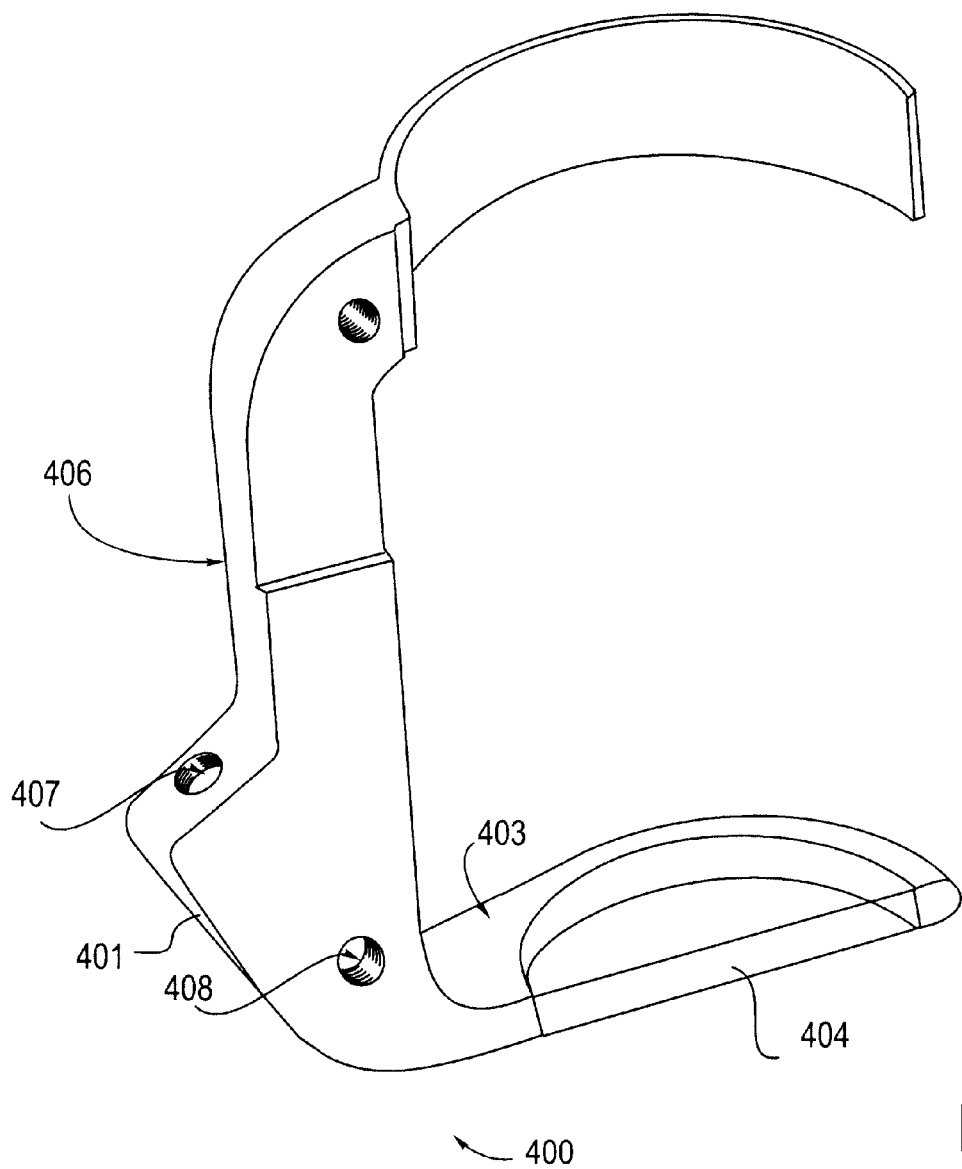
FIG. 5 is a view of an alternative embodiment of this invention.

In one embodiment of this invention, as depicted in FIG. 5, coolant is flowed through a small region 401 of device 400, in order to remove heat from window 404 via thermally conductive material 403. As shown in FIG. 5, even though a flowing coolant is used in this embodiment, the cost effectiveness is maintained by providing that the coolant flows only through a small portion 401 of the device, and not in a highly machined and expensive piping system surrounding window 404.

In one embodiment of this invention, as depicted in FIG. 5, coolant is flowed through a small region 401 of device 400, in order to remove heat from window 404 via thermally conductive material 403. Device 400 can be made from gold plated copper. As shown in FIG. 5, even though a flowing coolant is used in this embodiment, the cost effectiveness is maintained by providing that the coolant flows only through a small portion.401 of the device, and not in a highly machined and expensive piping system surrounding window 404. Specifically, handle 406 of device 400 is provided with one or more channels for providing a flow path not adjacent to, and thus spaced from, an edge of window 404. Coolant enters Such one or more channels through an inlet port 407 and exits handle 406 through an outlet port 408.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An apparatus for lowering the temperature of skin on a patient during treatment applying electromagnetic energy to the skin, comprising:
   a window of a first thermally conductive material through which electromagnetic energy can pass for placement against the epidermis of the skin;
   a reservoir of coolant spaced from an edge of said window; and
   a non-flowing second thermally conductive material connecting said window and said reservoir to transfer heat from said window to said coolant in said reservoir.

2. The apparatus of claim 1, wherein said second thermally conductive material at least partially surrounds said window.

3. The apparatus of claim 1, wherein said window is transparent to laser light.

4. The apparatus of claim 1, wherein said first thermally conductive material is substantially transparent in the wavelength range from 400 to 1100 nanometers and has good heat transfer properties.

5. The apparatus of claim 4, wherein said first thermally conductive material is selected from the group consisting of sapphire, quartz and polymorphic glass.

6. The apparatus of claim 1, wherein said coolant is selected from the group consisting of a liquid, water, air, nitrogen, $CO_2$, a cryogenic gas and ice water.

7. The apparatus of claim 1, wherein good thermal contact between said window and said second thermally conductive material is accomplished by brazing, bonding, gluing, soldering, or mechanically compressing said window to said second thermally conductive material.

8. The apparatus of claim 1, further comprising one or more temperature sensors in thermal contact with one or more of said window, said second thermally conductive material, and said reservoir.

9. The apparatus of claim 8, wherein at least one of said one or more temperature sensors is a color changing material.

10. The apparatus of claim 1, wherein said first thermally conductive material is substantially transparent to electromagnetic radiation between 0.2 and 3.5 microns and has good heat transfer properties.

11. The apparatus of claim 10, wherein said window is coated on one or more surfaces with an antireflection coating.

12. The apparatus of claim 10, wherein said first thermally conductive material is selected from the group consisting of diamond, sapphire, quartz and glass.

13. The apparatus of claim 1, wherein said first thermally conductive material is substantially transparent to radio-frequency and microwave radiation and has good heat transfer properties.

14. The apparatus of claim 13, wherein said window is coated on one or more surfaces with an antireflection coating.

15. The apparatus of claim 13, wherein said first thermally conductive material is selected from the group consisting of diamond, sapphire, quartz and glass.

16. An apparatus for use with a coolant to lower the temperature of skin on a patient during treatment applying electromagnetic energy to the skin, comprising:
   a window of a first thermally conductive material through which electromagnetic energy can pass for placement against the epidermis of the skin;
   a handle having one or more channels for receiving the coolant and providing a flow path spaced from an edge of said window; and
   a non-flowing second thermally conductive material connecting said window and said handle to transfer heat from said window to coolant contained in said one or more channels.

17. The apparatus of claim 16, wherein said second thermally conductive material at least partially surrounds said window.

18. The apparatus of claim 16, wherein said window is transparent to laser light.

19. The apparatus of claim 16, wherein said first thermally conductive material is substantially transparent in the wavelength range from 400 to 1100 nanometers and has good heat transfer properties.

20. The apparatus of claim 19, wherein said first thermally conductive material is selected from the group consisting of sapphire, quartz and polymorphic glass.

21. The apparatus of claim 16, wherein said coolant is selected from the group consisting of a liquid, water, air, nitrogen, $CO_2$, a cryogenic gas and ice water.

22. The apparatus of claim 16, wherein good thermal contact between said window and said second thermally conductive material is accomplished by brazing, bonding, gluing, soldering, or mechanically compressing said window to said second thermally conductive material.

23. The apparatus of claim 16, further comprising one or more temperature sensors in thermal contact with one or more of said window, said second thermally conductive material, and said one or more channels.

24. The apparatus of claim 23, wherein at least one of said one or more temperature sensors is a color changing material.

25. The apparatus of claim 23, further comprising a control device responsive to said one or more temperature sensors for adjusting the flow and/or temperature of coolant in said one or more channels.

26. The apparatus of claim 25, further comprising a refrigeration mechanism for cooling and recirculating said coolant.

27. The apparatus of claim 16, wherein said first thermally conductive material is substantially transparent to electromagnetic radiation between 0.2 and 3.5 microns and has good heat transfer properties.

28. The apparatus of claim 27, wherein said window is coated on one or more surfaces with an antireflection coating.

29. The apparatus of claim 27, wherein said first thermally conductive material is selected from the group consisting of diamond, sapphire, quartz and glass.

30. The apparatus of claim 16, wherein said first thermally conductive material is substantially transparent to radio-frequency and microwave radiation and has good heat transfer properties.

31. The apparatus of claim 30, wherein said window is coated on one or more surfaces with an antireflection coating.

32. The apparatus of claim 30, wherein said first thermally conductive material is selected from the group consisting of diamond, sapphire, quartz and glass.

33. The apparatus of 16 further comprising a refrigeration mechanism coupled to said handle for cooling and recirculating said coolant.

34. An apparatus for use with a coolant to lower the temperature of skin on a patient during a treatment applying laser energy to the skin, comprising a body of at least one nonflowing first thermally conductive material, a window of a second thermally conductive material through which the laser energy can pass attached to the body for placement against the epidermis of the skin, the body being provided with a flow channel through which the coolant can pass to transfer heat from the window and the body during the treatment.

35. The apparatus of claim 34 for use with a laser providing a laser beam wherein the body includes means for securing the laser to the body so that the laser beam passes through the window.

36. The apparatus of claim 35 wherein the second thermally conductive material is sapphire.

37. The apparatus of claim 36 wherein the body includes a layer of thermal epoxy in the vicinity of the window.

38. The apparatus of claim 34 wherein the body includes a handpiece.

* * * * *